(12) United States Patent
Wilson

(10) Patent No.: US 11,013,882 B1
(45) Date of Patent: May 25, 2021

(54) ANESTHETIC BREAST PAD

(71) Applicant: Joni Ann Wilson, Allen, TX (US)

(72) Inventor: Joni Ann Wilson, Allen, TX (US)

( * ) Notice: Subject to any disclaimer, the term of this patent is extended or adjusted under 35 U.S.C. 154(b) by 618 days.

(21) Appl. No.: 15/219,495

(22) Filed: Jul. 26, 2016

Related U.S. Application Data

(60) Provisional application No. 62/197,628, filed on Jul. 28, 2015.

(51) Int. Cl.
| | | |
|---|---|---|
| *A61F 13/14* | (2006.01) | |
| *A61M 19/00* | (2006.01) | |
| *A61M 35/00* | (2006.01) | |
| *A61F 13/15* | (2006.01) | |

(52) U.S. Cl.
CPC ............ *A61M 19/00* (2013.01); *A61M 35/00* (2013.01); *A61F 13/141* (2013.01); *A61F 2013/15016* (2013.01); *A61M 2202/048* (2013.01); *A61M 2210/1007* (2013.01)

(58) Field of Classification Search
CPC ......... A61M 19/00; A61M 35/00; A61F 7/00; A61F 13/14; A61F 13/141; A61F 2013/15016; A61F 2007/0019; A61F 2007/0021; A51B 3/00
See application file for complete search history.

(56) References Cited

U.S. PATENT DOCUMENTS

| | | | | |
|---|---|---|---|---|
| 5,679,052 A | * | 10/1997 | Rucki | ............ A61F 7/02 2/267 |
| 2002/0117169 A1 | * | 8/2002 | Kurz | ........... A61F 15/008 128/200.14 |
| 2003/0105445 A1 | * | 6/2003 | Lange | .......... A61F 13/141 604/385.07 |

OTHER PUBLICATIONS

Prajapati, et al. Topical Liposomes in Drug Delivery: A Review. Ganpat University. Jun. 2012. IJPRT vol. 4, No. 1. See attached.*

* cited by examiner

*Primary Examiner* — Catharine L Anderson
(74) *Attorney, Agent, or Firm* — Kenneth L. Tolar

(57) ABSTRACT

An anesthetic breast pad includes a polyester panel having a front surface, a rear surface, a continuous peripheral edge and a central aperture for accommodating a wearer's breast nipple. A sectoral notch extending from the peripheral edge to the central aperture allows the aperture and the panel to expand, contract and contort to comfortably adapt to the wearer. On the rear surface of the panel, along the entire peripheral edge, is an adhesive strip for tenuously securing the pad to the wearer. Within the boundary formed by the continuous adhesive strip is a thin sheet pretreated with a topical anesthetic. Accordingly, prior to surgery, a patient adhesively secures the pad to the breast to conveniently apply the anesthetic to the underlying area.

3 Claims, 2 Drawing Sheets

ANESTHETIC BREAST PAD

CROSS REFERENCE TO RELATED APPLICATIONS

This application is entitled to the benefit of provisional patent application No. 62/197,628 filed on Jul. 28, 2015, the specification of which is incorporated herein by reference.

BACKGROUND OF THE INVENTION

The present invention relates to an adhesive pad that conveniently applies a topical anesthetic to a cancer patient's breast prior to surgery.

DESCRIPTION OF THE PRIOR ART

A topical anesthetic is typically applied to a breast prior to surgery to minimize pain associated with shots and other preparatory medical instruments. In order to expedite the procedure, a physician often distributes an anesthetic cream to the patient beforehand so that the patient may apply it prior to appearing at a surgical facility. However, a conventional anesthetic cream is easily transferred to overlying clothing or other surfaces, which is annoying. Furthermore, if a portion of the cream is transferred to another surface, the breast may be inadequately desensitized.

Accordingly, there is currently a need for a means of more effectively applying a topical anesthetic to a patient's breast prior to surgery. The present invention addresses this need by providing a pad that conveniently applies a topical anesthetic to a breast when adhesively secured thereto.

SUMMARY OF THE INVENTION

An anesthetic breast pad comprises a polyester panel having a front surface, a rear surface, a continuous peripheral edge and a central aperture for accommodating a wearer's breast nipple. A sectoral notch extending from the peripheral edge to the central aperture allows the aperture and the panel to expand, contract and contort to comfortably adapt to the wearer. On the rear surface of the panel, along the entire peripheral edge, is an adhesive strip for tenuously securing the pad to the wearer. Within the boundary formed by the continuous adhesive strip is a thin sheet pretreated with a recommended dose of topical anesthetic. Accordingly, prior to surgery, a patient adhesively secures the pad to the breast to conveniently apply the anesthetic to the underlying area.

It is therefore an object of the present invention to provide an adhesive pad that conveniently applies a topical anesthetic to a cancer patient's breast prior to surgery.

It is therefore another object of the present invention to provide an anesthetic pad that eliminates the mess and inconvenience associated with applying conventional topical anesthetics to a breast.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
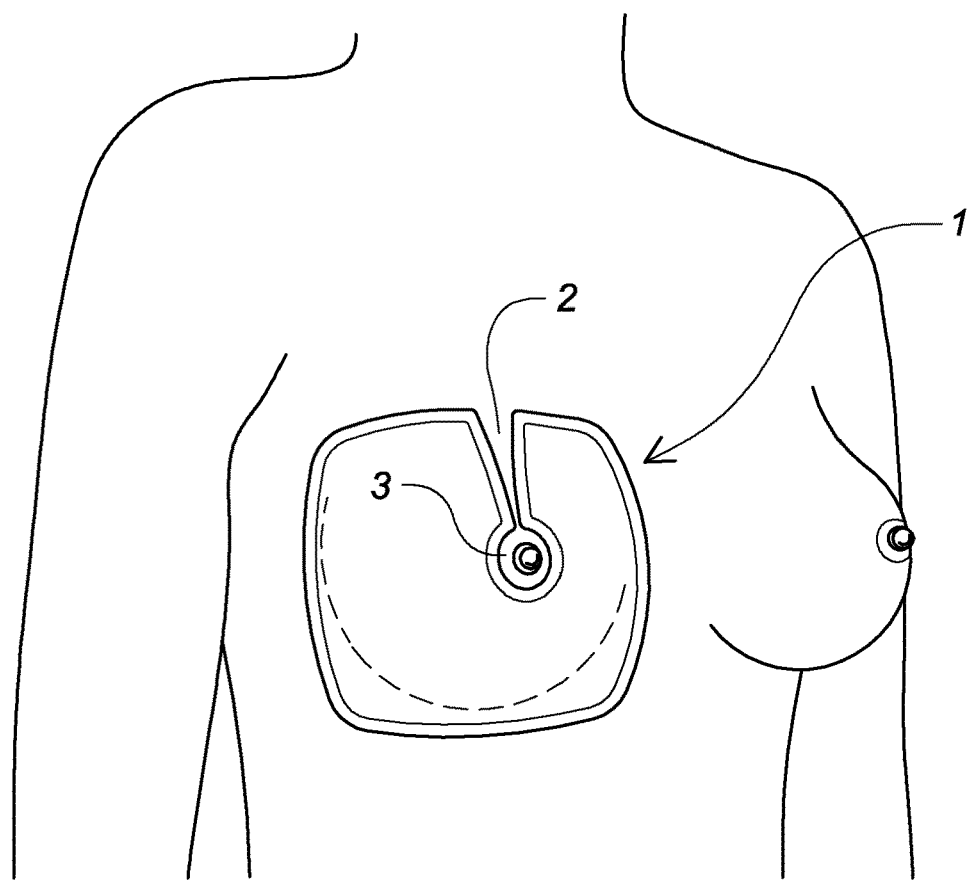
FIG. 1 depicts the anesthetic pad according to the present invention properly secured to a wearer's breast.
Figure 2:
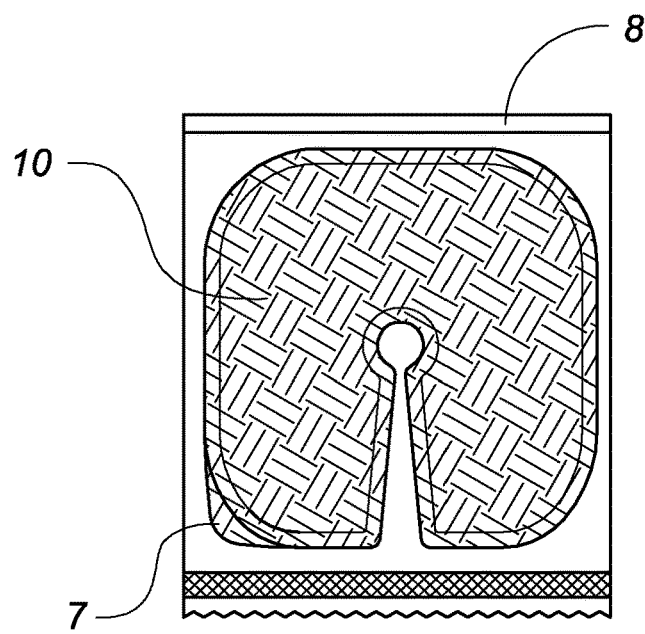
FIG. 2 depicts the anesthetic pad sealed within the protective cover.
Figure 3:
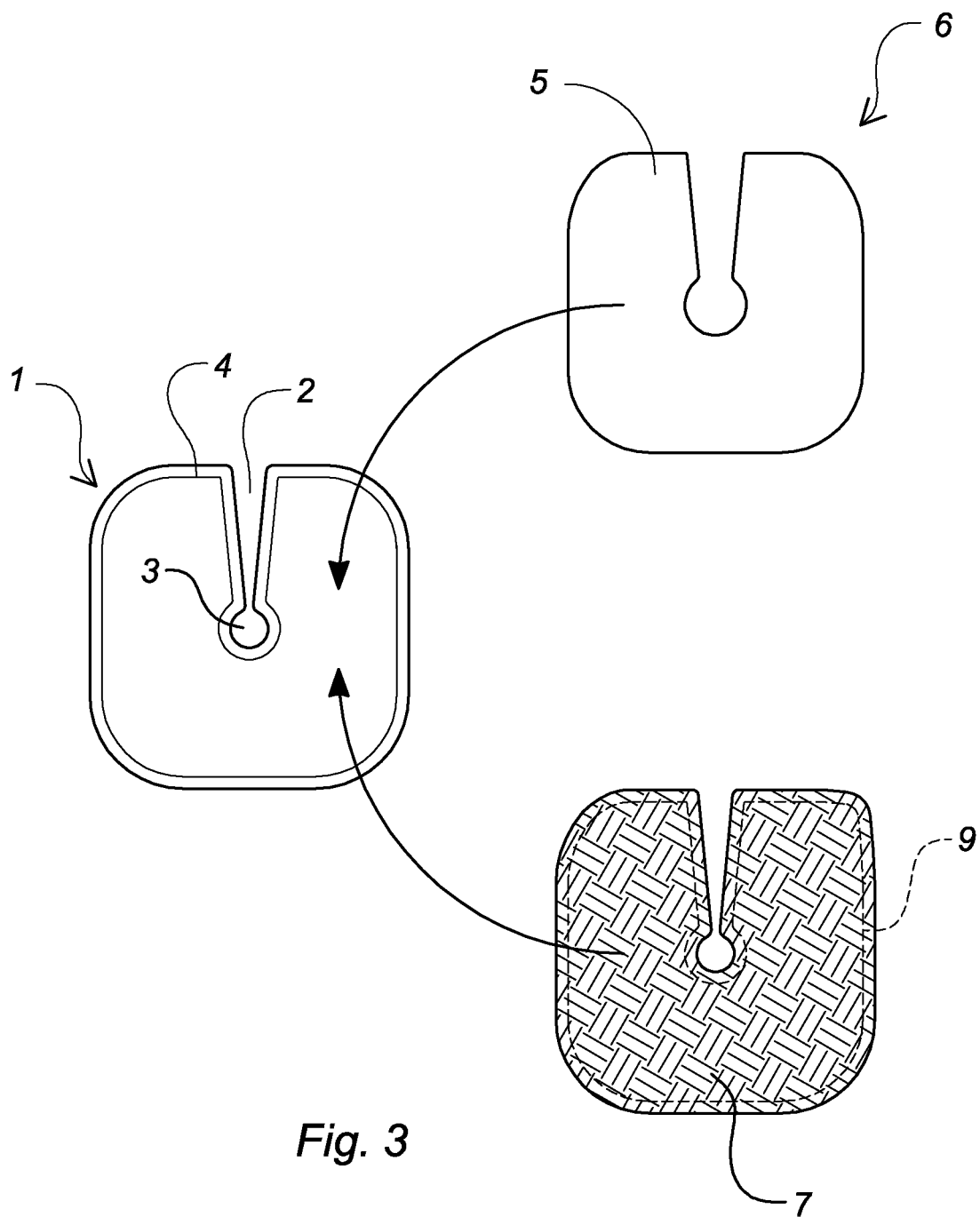
FIG. 3 is an exploded view of the anesthetic pad.

An anesthetic breast pad, generally identified as 10 in FIG. 1, comprises a polyester panel 1 having a front surface, a rear surface, a continuous peripheral edge and a central aperture 3 for accommodating a wearer's breast nipple. A sectoral notch 2 extending from the peripheral edge to the central aperture allows the aperture and the panel to expand, contract and contort to comfortably adapt to the wearer.

On the rear surface of the panel, along the entire peripheral edge, is an adhesive strip 4 for tenuously securing the pad to the wearer. Fastened to the rear surface of the panel, within the boundary formed by the continuous adhesive strip, is a thin sheet 6 having a substantially identical geometric configuration as the panel. An exposed surface 5 of the sheet is pretreated with a recommended dose of topical anesthetic, such as a cream or emollient mixture of lidocaine and prilocaine. Overlaying the sheet is a removable, protective layer 7 having a peripheral silicone strip 9 that is positioned to engage only the adhesive in order to protect the integrity of the anesthetic. The panel, the anesthetic sheet and the protective layer are hermetically sealed within a protective, disposable cover 8.

Accordingly, prior to surgery, a patient opens the cover to access the pad and removes the protective layer. The rear surface of the pad is adhesively secured to the breast to conveniently apply the anesthetic to the underlying area.

The above-described device is not limited to the exact details of construction and enumeration of parts provided herein. For example, though the topical anesthetic has been described herein as a mixture of lidocaine and prilocaine, virtually any known anesthetic cream or emollient may be used. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An anesthetic breast pad comprising:
    a panel having a front surface, a rear surface, a continuous peripheral edge and a central aperture for accommodating a wearer's breast nipple;
    a sectoral notch extending from the peripheral edge to the central aperture that allows the panel and aperture to expand, contract and contort to adapt to a wearer;
    a topical anesthetic on the rear surface of said panel;
    an adhesive strip on the rear surface of the panel, said adhesive strip extending along the entire peripheral edge, for securing the panel to the wearer;
    and a removable, protective layer overlaying said panel, said layer having a peripheral strip that is positioned to engage only with the adhesive strip in order to prevent destruction of the topical anesthetic.

2. The anesthetic breast pad according to claim 1 wherein said removable protective layer overlays the topical anesthetic.

3. An anesthetic breast pad comprising:
a panel having a front surface, a rear surface, a continuous peripheral edge and a central aperture for accommodating a wearer's breast nipple;
a sectoral notch extending from the peripheral edge to the central aperture that allows the panel to expand, contract and contort to comfortably adapt to a wearer;
an adhesive strip on the rear surface of the panel, said adhesive strip extending along the entire peripheral edge, for securing the panel to the wearer;
a thin sheet fastened to the rear surface of the panel, said sheet positioned within a boundary formed by the adhesive strip, said sheet having an exposed surface;
a topical anesthetic on the exposed surface of said sheet;
and a removable, protective layer overlaying said sheet, said layer having a peripheral strip that is positioned to engage only with the adhesive strip in order to prevent destruction of the topical anesthetic.

\* \* \* \* \*